United States Patent [19]

Präve et al.

[11] Patent Number: 4,545,945
[45] Date of Patent: Oct. 8, 1985

[54] PROCESS FOR IMPROVING THE GAS DISTRIBUTION IN AIR-LIFT LOOP REACTORS

[75] Inventors: Paul Präve, Bad Soden am Taunus; Wolfgang Sittig, Hofheim am Taunus, both of Fed. Rep. of Germany

[73] Assignee: Hoechst Aktiengesellschaft, Frankfurt, Fed. Rep. of Germany

[21] Appl. No.: 329,886

[22] Filed: Dec. 11, 1981

[30] Foreign Application Priority Data

Dec. 13, 1980 [DE] Fed. Rep. of Germany ....... 3047101

[51] Int. Cl.$^4$ ............................................. B01F 3/04
[52] U.S. Cl. .................................. 261/36 R; 261/77; 261/123; 422/227; 422/231; 435/314
[58] Field of Search ............... 261/36 R, 77, 123, 124; 422/227, 231; 435/313, 314

[56] References Cited

U.S. PATENT DOCUMENTS

| | | | |
|---|---|---|---|
| 642,460 | 1/1900 | Kersten | 261/77 X |
| 1,404,701 | 1/1922 | Pfisterer | 261/77 X |
| 2,188,192 | 1/1940 | Scholler et al. | 435/314 X |
| 2,715,521 | 8/1955 | Tatibana | 261/77 X |
| 3,630,848 | 12/1971 | Lefrancois | 435/314 X |
| 3,790,141 | 2/1974 | Champeau | 261/77 |
| 3,910,826 | 10/1975 | Kataoka | 261/77 X |
| 3,931,370 | 1/1976 | Murphy | 261/123 X |

FOREIGN PATENT DOCUMENTS

| | | | |
|---|---|---|---|
| 720884 | 7/1931 | France | 261/77 |
| 680753 | 9/1979 | U.S.S.R. | 261/77 |

Primary Examiner—Richard L. Chiesa
Attorney, Agent, or Firm—Curtis, Morris & Safford

[57] ABSTRACT

In a process for improving the gas distribution in air-lift loop reactors, the back-flowing, partially degassed liquid is divided into part streams prior to, during or after entry into the rising part of the loop. In this process, the cross-section of the sum of the part streams is intended to be smaller than the free cross-section of the rising part. The gas is passed into the part streams.

6 Claims, 1 Drawing Figure

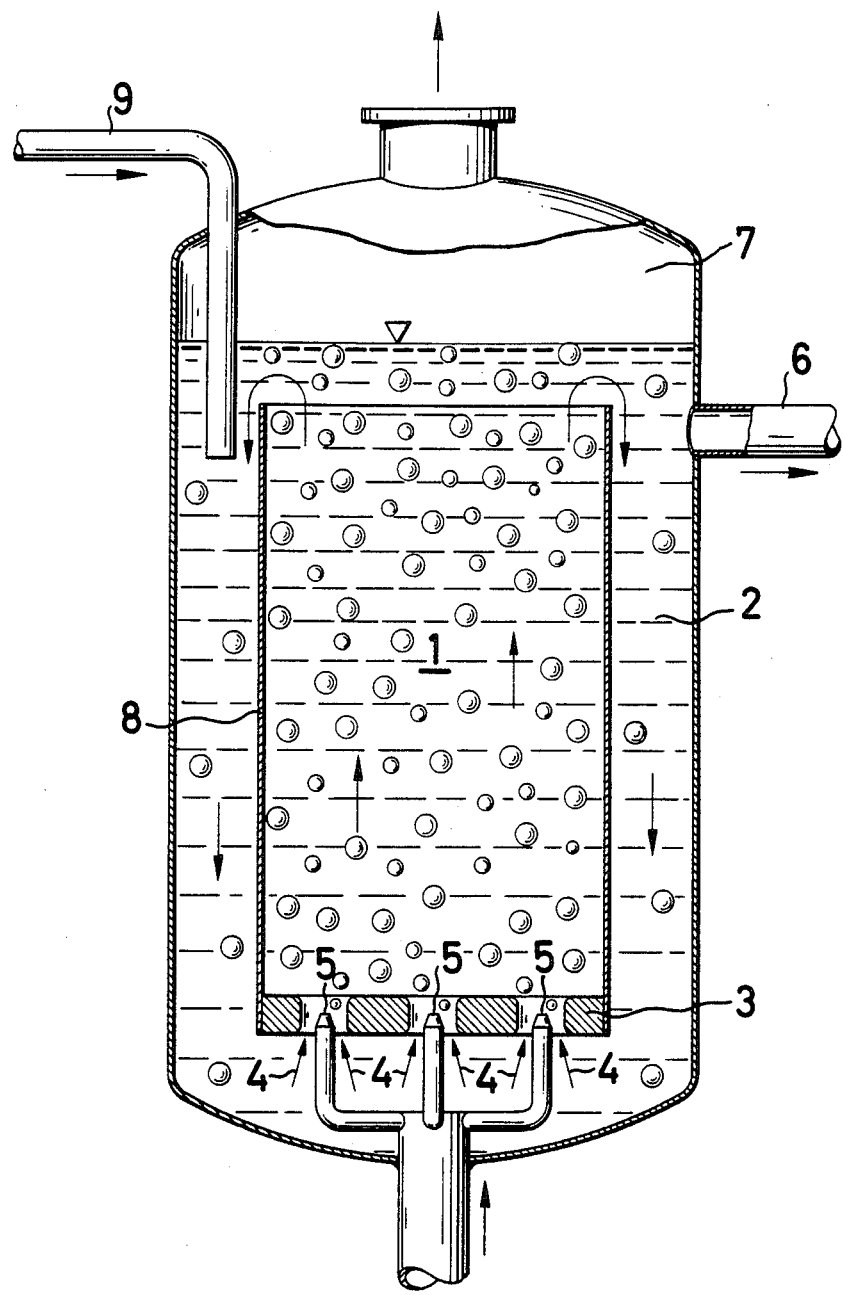

PROCESS FOR IMPROVING THE GAS DISTRIBUTION IN AIR-LIFT LOOP REACTORS

This invention relates to a process for improving the gas distribution in air-lift loop reactors.

Gas-liquid reactions are known in which the liquids are passed in a loop. It is also known to propel liquids with a gas. Reactors which are used for this purpose are known as air-lift or mammoth loop reactors. The gas flowing through the liquid and propelling it is distributed in the liquid, for example by means of simple nozzles, ring nozzles, nozzle rings, stirrers with gas outlets, jet nozzles, ejector nozzles, injector nozzles, spherical nozzles and the like. It is also known that the generation of bubbles and the effectiveness of the bubble distribution can be improved by using several outlet organs and/or by supplying additional external energy.

In the arrangement of several gas outlet organs distributed across the reactor cross-section lies the danger that successively issuing bubbles form a chain, so that bubbles following in the wake of bubbles rising ahead of them are accelerated, catch up with the latter and fuse with them, so that the available mass transfer area is reduced. An additional supply of energy, for example in the form of liquids, to the gas outlet points has the effect of reducing the bubble size by stripping the bubble from the outlet orifice relatively soon and of quickly mixing the bubbles with a relatively large volume of liquid. The probability of bubble contact and hence the rate of coalescence is thereby lowered. However, additional energy makes processes of this type less economical.

The object of the present invention is therefore to supply an energy-rich stream of liquid to all gas inlet points, without using additional energy for propelling the liquid.

The object is achieved by a process which comprises dividing the back-flowing, partially degassed liquid into part streams prior to, during or after entry into the rising part of the loop, the cross-section of the sum of the part streams being smaller than the free cross-section of the rising part, and passing the gas into the part streams. In this process the sum of the cross-sections of the individual part streams can advantageously be 0.05 to 0.8 times the free cross-section of the rising part of the loop. This corresponds to liquid velocities at a gas inlet of 4 to 100 m.sec$^{-1}$. If the reaction requires other components, for example catalysts, it is advantageous to introduce these into the liquid likewise at the gas inlet points. It can be advantageous in particular cases further to increase the achieved velocities of the part streams by means of a liquid jet or by mechanical means. It can also be advantageous to divide into part streams, and to pass these to the gas inlet points, only a part of the partially degassed liquid flowing downwards in the downflow part.

The invention will now be explained in greater detail with the aid of the diagrammatic representation: A liquid is passed through the line (9) to and, through the line (6), away from an air-lift loop reactor, the cylindrical or annular-shaped or rectangular, gas-fed rising space (1) of which is separated off by a guide device (8) from an annular-shaped or cylindrical or rectangular down-flow part (2) to which no gas or only a small amount of gas is fed and the upper part of which reactor is shaped as a gas separation zone (7). Gas is fed in preferably at the lower end of the rising space (1). The partially degassed down-flowing liquid in the down-flow space (2) is dammed, by inserts (3), prior to or during entry into the lower part of the rising space (1) and divided into as many high velocity part streams (4) as there are gas inlet points (5). Each part stream (4) is introduced into the rising space (1) at a gas inlet point (5) each and mixed with the gas stream, whereby the latter is distributed in the rising space. It is advantageous to design the gas inlet point in the form of a nozzle and to introduce the part gas stream and the gas into the liquid at that point where the part streams have their highest velocity.

EXAMPLE 1

Air is fed at a rate of 192 m$^3$/h into a loop reactor which has a cylindrical cross-section with a diameter of 600 mm and a depth of liquid of 1.70 m, a concentric inner tube with a diameter of 400 mm as rising space and an annulus as down-flow space. An oxygen transfer coefficient of 210 h$^{-1}$ could be achieved when three gas-feeding nozzles were used; when using a device according to the invention the transfer coefficient was 260 h$^{-1}$.

EXAMPLE 2

For the fermentation of *Trichoderma viride*, as the gas was fed at a rate of 300 m$^3$/h into a loop reactor which had a diameter of 600 mm, a depth of liquid of 10 m and a guide tube diameter of 500 mm, and which achieved an oxygen feed-in rate of 11 kg/h when the gas was fed in via a ring nozzle. The same supply of air, at a rate of 300 m$^3$/h, achieved an oxygen feed-in rate of 15 kg/h when three air nozzles were used which had been arranged, according to the invention, within 3 liquid nozzles which had a narrowest cross-section of 150 mm.

EXAMPLE 3

A loop reactor which had a diameter of 1600 mm, a depth of gas-fed liquid of 17 m and an interior tube diameter of 1300 mm, was used for fermentation of *Methylomonas clara*. The nutrient solution contained:

| | | |
|---|---|---|
| 0.2% | of a 75% H$_3$PO$_4$ solution | (technically pure) |
| 0.117% | of K$_2$SO$_4$ | (technically pure) |
| 0.08% | of MgSO$_4$.7H$_2$O | (technically pure) |
| 0.003% | of FeSO$_4$.7H$_2$O | (technically pure) |
| 0.024% | of Na$_2$SO$_4$ | (technically pure) |
| 0.0001% (pH 2–3) | of trace elements | (technically pure) |
| 0.3% | of a pH-controlled 25% solution of NH$_3$ in water | |
| 0.1% | and of methanol. | |

The nutrient solution was metered at a dilution rate of 0.23 h$^{-1}$, and the amount of culture which overflowed was harvested continuously. When a conventional ring nozzle with a diameter of 80 mm and a slot of 8 mm was used, an oxygen feed-in rate of 120 kg/h was achieved and the amount of fresh air metered in was 1700 m$^3$/h. Biomass was produced at a rate of 69 kg/h. By dividing the degassed stream of liquid into 7 part streams, in accordance with the invention, and with a reduction of the cross-section to 0.04 m$^2$ per part stream, and distributing the gas into 7 part streams of 240 m$^3$/h each, an oxygen feed-in rate of 160 kg/h and a production rate of 92 kg/h were achieved. The fermentation temperature was 39° C., and the pH was 6.8.

We claim:

1. A process for improving the gas distribution in air-lift loop reactors of the type in which gas is supplied to a reactor vessel through multiple-outlet gas nozzle means disposed in a lower portion of the vessel and having a predetermined plurality of gas outlets, and a guide device disposed above the gas nozzle means separates liquid in the vessel into an upflow space in which gassed liquid rises to a degassing zone and a downflow space in which partially degassed liquid flows down to below the guide device, the guide device defining a free cross section for the rising gassed liquid in the upflow space; comprising the steps of damming said free cross section of said upflow space with damming means at the location of said gas nozzle means; providing a corresponding predetermined plurality of apertures in said damming means to define part streams at said damming means flowing therethrough into said upflow space, said liquid entering said upflow space only through said apertures with each aperture being associated with a respective one of said gas outlets disposed thereat, and the part streams having cross sections such that the sum of the cross sections of the part streams is less than the free cross section of the upflow space; and introducing gas through said gas outlets into said part streams.

2. A process as claimed in claim 1, wherein the sum of the cross-sections of the part streams is 0.05 to 0.8 times the free cross-section of the upflow space.

3. A process as claimed in either claim 1 or 2, wherein the velocities of the part streams which can be achieved by the effect of the air-lift pump are increased by means supplying additional external energy.

4. A process as claimed in claims 1 or 2, wherein further components are passed into the part streams at the gas inlet points.

5. A process as claimed in claim 4, wherein the velocities of the part streams which can be achieved by the effect of the nozzle means are increased by means supplying additional external energy.

6. A process as claimed in claim 1, wherein said step of passing gas through said gas outlets into said part streams includes introducing the gas into the liquid at a point where the part streams attain their maximum velocity.

* * * * *